(12) United States Patent
Childre et al.

(10) Patent No.: US 7,117,032 B2
(45) Date of Patent: Oct. 3, 2006

(54) SYSTEMS AND METHODS FOR FACILITATING PHYSIOLOGICAL COHERENCE USING RESPIRATION TRAINING

(75) Inventors: Doc L. Childre, Boulder Creek, CA (US); Rollin I. McCraty, Boulder Creek, CA (US); Michael A. Atkinson, Boulder Creek, CA (US)

(73) Assignee: Quantum Intech, Inc., Boulder Creek, CA (US)

( * ) Notice: Subject to any disclaimer, the term of this patent is extended or adjusted under 35 U.S.C. 154(b) by 0 days.

(21) Appl. No.: 10/983,138

(22) Filed: Nov. 4, 2004

(65) Prior Publication Data

US 2005/0124906 A1    Jun. 9, 2005

Related U.S. Application Data

(63) Continuation-in-part of application No. 10/486,775, filed as application No. PCT/US00/05224 on Mar. 1, 2000, which is a continuation of application No. 09/260,463, filed on Mar. 2, 1999, now Pat. No. 6,358,201.

(60) Provisional application No. 60/517,534, filed on Nov. 8, 2003.

(51) Int. Cl.
*A61B 5/04* (2006.01)
*A61B 5/08* (2006.01)

(52) U.S. Cl. ................. 600/545; 600/544; 600/529

(58) Field of Classification Search ............... None
See application file for complete search history.

(56) References Cited

U.S. PATENT DOCUMENTS

| | | | | |
|---|---|---|---|---|
| 5,694,939 A | * | 12/1997 | Cowings | 600/484 |
| 5,800,337 A | * | 9/1998 | Gavish | 600/27 |
| 6,067,468 A | * | 5/2000 | Korenman et al. | 600/547 |
| 6,554,763 B1 | * | 4/2003 | Amano et al. | 600/26 |
| 6,662,032 B1 | | 12/2003 | Gavish et al. | |
| 2003/0171643 A1 | * | 9/2003 | Nobuchi et al. | 600/26 |

* cited by examiner

*Primary Examiner*—Robert L. Nasser
(74) *Attorney, Agent, or Firm*—Crowell & Moring LLP

(57) ABSTRACT

Systems and methods for facilitating physiological coherence using respiratory training are disclosed. In one embodiment, an optimal respiratory cycle and/or RSA pattern is determined. A subject is then trained to adhere to this optimal respiratory level using one or more breath indicators. In another embodiment, the timing sequence of the breath indicators is optimized for a given subject's reaction time and/or atypical breathing events. In yet another embodiment, a subject's respiratory rhythms are used to detect their emotional state and corresponding feedback provided.

32 Claims, 5 Drawing Sheets

SYSTEMS AND METHODS FOR FACILITATING PHYSIOLOGICAL COHERENCE USING RESPIRATION TRAINING

CROSS REFERENCE TO RELATED APPLICATION

This application is related to and claims the benefit of U.S. Provisional Patent Application No. 60/517,534, filed on Nov. 8, 2003, which is hereby fully incorporated by reference. This application is also a continuation-in-part of U.S. patent application Ser. No. 10/486,775 filed on Feb. 13, 2004 which is based upon PCT International Application No. PCT/US00/05224, filed on Mar. 1, 2000, which is a continuation of U.S. patent application Ser. No. 09/260,643, filed on Mar. 2, 1999 now U.S. Pat. No. 6,358,201, which is hereby fully incorporated by reference.

BACKGROUND OF THE INVENTION

1. Field of the Invention

The invention relates to facilitating physiological coherence (also referred to as entrainment or resonance) and more particularly, to systems and methods for using respiration-training or mental/emotional self-management techniques to achieve physiological coherence and/or entrainment. Systems and methods for monitoring respiration patterns to detect emotional/stress state are also disclosed.

2. Background of the invention

With the growing complexity of life, the relation between physiological conditions and emotional health becomes of increasing interest and importance. Many studies have shown that stress and other emotional factors increase the risk of disease, reduce performance and productivity and severely restrict the quality of life. To this end, the medical communities around the world continually seek remedies and preventive plans. Recently, a focus on the self-regulation of systems within the body has led to research in the areas of increasing performance and facilitating recovery from numerous health challenges. Such research has suggested a causal link to, for example, enhanced academic performance, communication and listening skills, faster reaction times and better coordination.

In the last 25 years, a variety of new techniques have been introduced as alternatives to more traditional psychotherapies or pharmaceutical interventions for improving mental and/or emotional imbalances, reducing stress and improving performance. In addition to the more psychological approaches like cognitive re-structuring and neurolinguistic programming, psychologists have employed several techniques from Eastern cultures to "still the mind" during focused meditation. In yoga, for example, one generally focuses on the breath or parts of the brain, whereas in qigong one focuses on the "dan tien" point (below the navel). In the Freeze Frame® (FF) and other related techniques, developed by the Institute of Heart Math in Boulder Creek, Calif., one focuses attention on the area around the heart. All these techniques focus attention upon areas of the body which are known to contain separate but interacting groups of neuronal processing centers, and biological oscillators with which they interact. The heart, brain, and the intestines contain biological oscillators known as pacemaker cells. By intentionally focusing attention on any one of these oscillator systems, one can alter its rhythms. This is at least true for the brain (meditation), yogic breathing (respiration) and other cognitively-directed paced-breathing techniques, the heart (Freeze-Framer (FF) and other HeartMath techniques), and most likely the gut (qigong). The body also contains other oscillating systems such as the smooth muscles of the vascular system. In U.S. Pat. No. 6,358,201, entitled "Method and Apparatus for Facilitating Physiological Coherence and Autonomic Balance," which is assigned to the assignee hereof and hereby incorporated fully by reference, it was shown that the body's systems such as blood pressure rhythms (measured by recording pulse transit time (PTT), the heart (measured by a heart rate variability (HRV)), and the respiration system (measured by the respiration rate) can all entrain. Furthermore, they all synchronize to a frequency varying around 0.1 Hertz (Hz). Thus, one can intentionally bring these systems, acting as coupled biological oscillators, into synchronization with each other. In addition, in this coherent or resonant mode, several brain rhythms (measured by an electroencephalograph (EEG)) become more synchronized to the heart.

By applying spectral analysis techniques to the HRV waveform, its different frequency components, which represent the activity of the sympathetic or parasympathetic branches of the autonomic nervous system, can be discerned. The HRV power spectrum is divided into three frequency ranges or bands: very low frequency (VLF), 0.033 to 0.04 Hz; low frequency (LF), 0.04 to 0.15 Hz; and high frequency (HF), 0.15 to 0.4 Hz.

The high frequency (HF) band is widely accepted as a measure of parasympathetic or vagal activity. The peak in this band corresponds to the heart rate variations related to the respiratory cycle, commonly referred to as respiratory sinus arrhythmia (RSA). Reduced parasympathetic activity has been found in individuals under mental or emotional stress, suffering from panic, anxiety or worry, depression, high blood pressure, heart disease and many other disorders. As such, previous RSA training approaches have focused on increasing the HF peak in the HRV power spectrum. The low frequency (LF) region can reflect both sympathetic and parasympathetic activity, especially in short-term recordings.

While the FF technique described in previously incorporated U.S. Pat. No. 6,358,291 is a self-management technique which focuses on the heart, the respiratory cycle may also be linked to mental/emotional state and can be used to achieve physiological coherence and/or entrainment. Thus, there is a need to provide a method and apparatus for optimizing the respiratory cycle and RSA pattern in a manner that facilitates physiological coherence.

BRIEF SUMMARY OF THE INVENTION

Methods and apparatus for facilitating physiological coherence using respiratory monitoring and training are disclosed. In one embodiment, a method for improving human emotional states includes monitoring a subject's respiration, and determining one or more current breathing patterns for the subject, where the one or more current breathing patterns include at least one of a current respiratory cycle and a current respiratory sinus arrhythmia pattern. The method also includes determining one or more optimal breathing patterns for the subject, where the one or more optimal breathing patterns also include at least one of an optimal respiratory cycle and an optimal respiratory sinus arrhythmia pattern. In one embodiment, the method further includes prompting the subject to take a breath at a specific time to cause the one or more current breathing patterns to approximate the one or more optimal breathing patterns, and providing feedback to the subject representative of the subject's emotional state.

Other embodiments are disclosed and claimed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF EXEMPLARY EMBODIMENTS

I. Background

Figure 1:
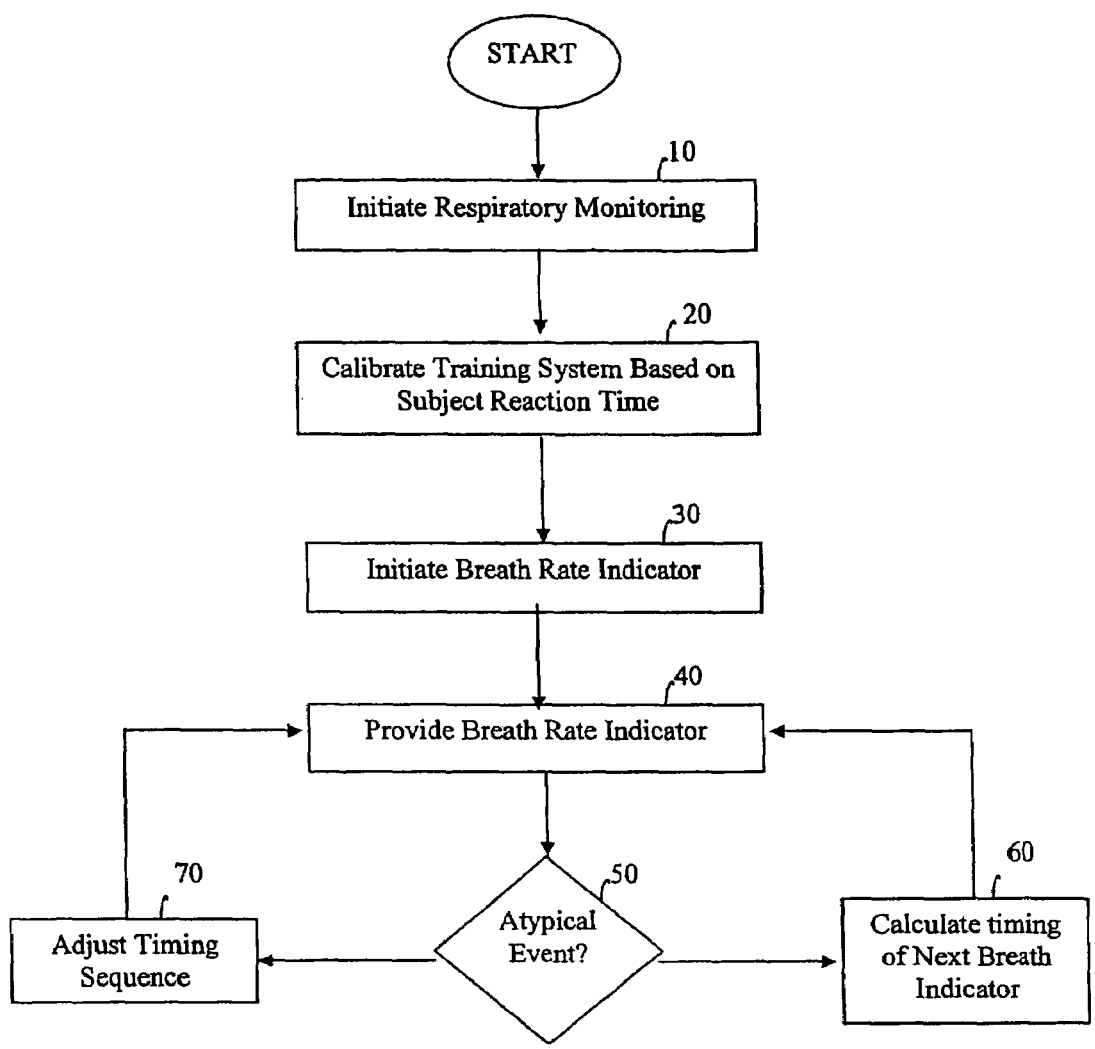
FIG. 1 illustrates a flow diagram of a training process according to one embodiment.

As disclosed in the previously-incorporated U.S. Pat. No. 6,358,201, Freeze-Frame® is one tool that may be used for mental and emotional self-management and performance enhancement. It consists of consciously disengaging the mental and emotional reactions to either external or internal events and then shifting one's center of attention to the physical area around the heart and breathing as if you are breathing through the heart at a rhythm of 5 seconds on the in-breath and 5 seconds on the out-breath as if you are breathing out through the solar plexus. These steps facilitate a shift in the heart's rhythmic beating pattern. The next step is to intentionally shift one's emotional state by focusing on a positive emotion such as love, care or appreciation. In one embodiment, this emotional shift stabilizes the coherent physiological mode and takes the process past what can be achieved with breathing techniques alone. This tool thus allows the individual to shift focus of attention from the mind to the heart. Such a shift results in a wider and more objective perception in the moment.

One embodiment of the present disclosure relates to a training system designed to optimize the respiratory cycle. In one embodiment, by optimizing the respiratory cycle to facilitate coherence and resonance, a subject's emotional state, stress levels and performance may be concurrently improved.

We use the term "coherence" in a broad context to describe more ordered mental and emotional processes as well as more ordered and harmonious interactions among various physiological systems. In this context, "coherence" embraces many other terms that are used to describe specific functional modes, such as synchronization, entrainment, and resonance.

Physiological coherence is characterized by both autocoherence and cross-coherence in the activity of physiological systems. For example, this mode is associated with increased coherence in breathing rhythms and the heart's rhythmic activity, which manifests as a sine wave-like heart rhythm pattern (autocoherence). Additionally, during this mode there also tends to be increased cross-coherence or entrainment among different physiological oscillatory systems, including the heart rhythms, respiratory rhythms, and blood pressure waves.

A related phenomenon that occurs during physiological coherence is resonance. In physics, resonance refers to a phenomenon whereby an unusually large vibration is produced in a system in response to a stimulus whose frequency is the same as, or nearly the same as, the natural vibratory frequency of the system. The frequency of the vibration produced in such a state is said to be the resonant frequency of the system. When the human system is operating in the coherent mode, increased synchronization occurs between the sympathetic and parasympathetic branches of the ANS, and entrainment occurs among the heart rhythms, respiratory rhythms, and blood pressure oscillations and can also occur among very low-frequency brain rhythms, craniosacral rhythms, and electrical potentials measured almost anywhere across the skin. This occurs because these oscillatory subsystems are all vibrating at the resonant frequency of the system (~0.1 Hertz). Thus, in the coherent mode, the power spectrum of the heart rhythm displays an unusually large peak around 0.1. Most models show that the resonant frequency of the human cardiovascular system is determined by the feedback loops between the heart and brain. In humans and in many animals, the resonant frequency of the system is approximately 0.1 Hertz, which is equivalent to a 10-second rhythm.

In terms of physiological functioning, physiological coherence or resonance confers a number of benefits to the system. For example, there is increased cardiac output in conjunction with increased efficiency in fluid exchange, filtration, and absorption between the capillaries and tissues; increased ability of the cardiovascular system to adapt to circulatory requirements; and increased temporal synchronization of cells throughout the body. This results in increased system-wide energy efficiency and metabolic energy savings. These findings provide a link between positive emotions and increased physiological efficiency, which may partly explain the growing number of correlations documented between positive emotions, improved health, and increased longevity.

It is possible to have entrainment between the heart rhythm and respiration without entrainment with other physiological systems. This can occur in the high frequency range of the HRV power spectrum, which is associated with respiratory sinus arrhythmia (RSA). Although this type of entrainment represents a more ordered form of RSA, it is not reflective of the more system-wide coherence or resonance that we are describing here. Respiratory sinus arrhythmia biofeedback training has focused on increasing the amount of HRV in the high frequency region of the power spectrum. The process described here is fundamentally different as it facilitates the coherent or resonant physiological mode.

The respiratory rhythm can be utilized to facilitate coherence because it modulates the heart rhythm. This is why taking a few deep breaths during a stressful time can be helpful because breathing patterns modulate heart rhythms and heart rhythms have powerful body-wide effects, including a change in the afferent neural patterns sent to the brain from the heart. However, for the coherent mode to emerge, the breathing rate should be at the correct frequency.

The nervous system mechanisms coupling breathing and heart rhythms are complex and there is no universal understanding as to the mechanisms underlying the generation of RSA. Autonomic response systems are continuously being updated and regulated via complex feedback systems. These feedback loops, typical of many regulatory processes, produce a rhythmic pattern characterized by phasic increases and decreases in neural efferent and afferent activity between organs such as the lungs, heart and brain. Often, as in the case of heart rate, there are numerous feedback influences and, thus, the response is composed of the sum of numerous rhythmic components. Within normal parameters, greater amplitude of oscillation is associated with health. Thus, the amplitude of rhythmic physiological processes may index the status of the individual's nervous system and capacity to respond. In other words, the greater the amplitude of "organized" rhythmic physiological variability, the greater the response potential or possible range of behavior.

The three primary mechanisms generally proposed to explain the modulation of heart rate associated with respiration are: (1) a direct influence of medullary respiratory neurons on cardiomotor neurons; (2) an indirect influence on heart rate of blood pressure changes secondary to respiratory movements that is mediated via arterial baroreceptors or atrial stretch receptors; and (3) a reflex response to lung inflation mediated by thoracic stretch receptors, most likely from the lungs and chest wall.

Although both supportive and contrary evidence exists for most of the mechanisms listed above, it is likely that each of them plays at least some role in generating RSA. Thus, RSA reflects the complex effects of central respiratory drive on the integration of autonomic afferent signals and the production of autonomic efferent signals in the brain stem, and of respiratory mechanics on the cardiovascular structures within the thorax. The phenomenon is dependent on the frequency and amplitude of respiration, as well as on the underlying autonomic state of the organism. The magnitude and phase characteristics of RSA during different physiological states suggest that it is mediated by respiratory modulation of both cardiac sympathetic and vagal efferent activity, and mechanical stretch of the lungs.

The fact that respiration modulates the heart rhythm makes it a powerful intervention that can have quick and profound body-wide effects, if it is used to drive the coherent mode and this requires knowing the appropriate breathing rate.

We have found that as the respiratory rate is lowered, there is a point at which the heart rate variability pattern, blood pressure rhythm and respiratory rhythms suddenly entrain. In essence, the system shifts modes and operates at its resonance frequency. As described in previously-incorporated U.S. Pat. No. 6,358,201, this frequency is around 0.01 Hz for most people. However, there is a range of frequencies between 0.03125 Hertz and 0.234 Hertz in which the coherent mode can be observed in the majority of people. When a person is functioning in the coherent mode, there is a variability in the non-linear rhythms (respiratory, blood pressure or heart rhythm) that is typically in the range of 0.03125 Hertz. In terms of respiration, this would mean we would expect the rhythm to vary about one breath per minute around each side of the resonant frequency which is typically a ten second rhythm (0.1 Hertz).

As used hereafter, the term "appreciation" shall mean the state in which the subject has clear perception or recognition of the feelings of sincere or active appreciation for someone or something. It is the heart-felt feeling of appreciation that is associated with the HRV and/or respiratory cycle changes. As with any experiential state, it is difficult to find words that adequately describe it. However, with practice the ratios of time in this state can be increased. It can also be described as similar to those moments that one sometimes has when at the beach or in the forest when one feels an especially deep contact with nature or with oneself that is beyond one's normal experience. It is often in these moments that we find the answers to the deeper issues or problems that we experience.

By the term "biological oscillators" we mean cells or groups of cells that produce rhythmic oscillation. When the instantaneous systemic arterial pressure is continuously recorded, fluctuations with each heart beat and with each breath are seen. This rhythmic activity in the autonomic nervous system appears to be supported by at least three biological oscillator systems: 1) centrogenic rhythms in brainstem networks with facultative coupling (entrainment) with the respiratory oscillator, 2) the baroreceptor feedback network, and 3) the autorhythmicity of the vascular smooth muscle. The fact that each of the oscillators can develop different frequencies and that the phase lags between the oscillations explains the frequency pulling that can occur between the physiological oscillators, with similar basic frequencies enabling synchronization and entrainment between oscillators.

Arterial pulse transit time (PTT) is a measure of the speed of travel of the arterial pulse wave from the heart to some peripheral recording site. It is used as a non-invasive method to monitor the elasticity of the artery walls, to indicate changes in blood pressure on a beat-to-beat basis and to indicate changes in the blood pressure rhythm.

As used herein, physiological coherence is characterized by a narrow band high amplitude signal in the LF region of the HRV power spectrum, with no other significant peaks in the VLF or HF region, and a relatively harmonic signal (sine-wave-like), in the time domain trace of the HRV data.

II. Respiratory Cycle Training

As previously mentioned, while the respiratory cycle and RSA amplitude has been known to be linked to physical and emotional health, there is a need for an improved method for optimizing the respiratory cycle and RSA pattern in a manner that facilitates physiological coherence.

In one embodiment, an optimal number of breaths per minute is determined from the height of the coherence peak in the HRV power spectrum and/or the stability and height of the spectrum of the respiration trace. In another embodiment, an optimal pattern and frequency of breaths per minute may be determined and used to train a given subject. For example, anxiety and depression will have typical breathing patterns that could be detected as would other types of stress, e.g. sadness, frustration, anger. Different positive emotions, such as love, compassion, care or joy will also have typical breathing patterns. These can be detected from the HRV, the breathing pattern or a combination thereof. It should equally be appreciated that the optimal number of breaths (or range) may be determined for any given period of time (e.g., per second). As previously mentioned, in one embodiment this optimal number of breaths is the point at which the HRV pattern, blood pressure rhythm and respiratory rhythm entrain (referred to herein as the resonant frequency). While this frequency may be approximately 0.1 Hz, in another embodiment, the resonant frequency may be in the range of between 0.03125 Hertz and 0.234 Hertz.

Once a subject's emotional state has been determined, a respiratory cycle training system may be used to achieve a state of entrainment and/or coherence. In one embodiment, the respiratory cycle training system includes a breath indicator that may be used to identify when a subject should take their next breath. The breath indicator may also function as a prompt for the subject signaling that a breath should be taken. Regardless of the type of breath indicator used, in one embodiment the indicator timing sequence is a function of the predetermined optimal number of breaths. By way of a non-limiting example, if the predetermined optimal number of breaths is determined to be 6 breaths per minute, then the timing sequence for the breathing indicator would be set to 10-second intervals. Thus, in this case a subject would be provided with a breath indicator at each 10-second interval such that a total of 6 breaths would be taken each minute. It should of course be appreciated that the predetermined optimal number of breaths per minute may be more or less than 6.

While the breath indicator may be any indication capable of perception using one or more of the human senses, in one embodiment the breath indicator is a light that is visible to a given subject. Based on the indicator timing sequence (which in turn is based on the optimal number of breaths per given time period), the light may be illuminated to indicate that the subject should take a breath. It should similarly be appreciated that any other visual prompt may be used.

In addition to (or instead of) a visual breath indicator, an audible indicator may be used to train the respiratory cycle of a given subject. In this case, the subject may be exposed to a particular sound at the moment the subject should take a breath.

The breath indicator may also be a tactile indicator that provides a tactile signal to the subject when a breath should be taken. In one embodiment, the tactile indicator may be a belt-type apparatus that is placed around a subject's torso. When the breath timing sequence calls for the subject to take a breath, the belt-type apparatus may vibrate or be slightly constricted, thereby prompting the subject to take a breath.

In order to fully optimize a subject's respiratory cycle, the subject's reaction time to the breathing stimulus may also be taken into account. That is, the time between when the breath indicator is provided to the subject and the time when the subject actually takes a breath may vary by 1–2 seconds. Moreover, reaction times tend to vary between subjects. Accordingly, the training system may be calibrated based on a particular subject's reaction time. In one embodiment, a calibration mode is used to determine an approximation of a given subject's reaction time. During this calibration mode, a series of breath indications are provided to the subject. The length of time between when the breath indications are provided and when the subject actually takes a breath may then be measured. This value is then incorporated into the indicator timing sequence to ensure that the optimal number of breaths per given time period (e.g., per minute) are taken.

Even after taking reaction times into account, many subjects will experience atypical breathing events from time to time (e.g., breath holding or not breathing out fully). While this may be caused by numerous factors, the result is often that the subject is not able to adhere to the indicator timing sequence. These atypical breathing events are typically involuntary and can include taking an extra breath or "quick breath," or not taking a breath when prompted to do so (e.g., may occur if the subject momentarily doses off). In any event, once an atypical breathing event occurs, the indicator timing sequence may not be optimized. Accordingly, it is another aspect of the invention to provide a training system which utilizes a feedback loop that adjusts the indicator timing sequence to take into account such atypical breathing events. To that end, the training system may utilize a breathing monitor to detect when the subject has taken a breath. In one embodiment, a vest or strap can be used to detect when the subject takes a breath.

Another aspect of the invention is to provide guidance and feedback that is correlated to either the respiratory or HRV rhythm in which a target pattern is displayed to the subject. In one embodiment, this target pattern is a sine wave of an optimized respiratory/HRV rhythm that the subject's respiratory/HRV rhythm should attempt to match.

In another embodiment, rather than representing the ideal or optimized rhythm, the frequency of the target pattern (e.g., sine wave) converges on the optimized frequency as the subject's "coherence peak" is maximized. When the coherence peak reaches its maximum, the frequency would be the natural resonant frequency that would become the target rhythm that may then be displayed to the subject for training purposes.

Referring now to the figures, FIG. 1 illustrates one embodiment for how a subject may be trained to optimize their respiratory cycle. The process begins at block 10 where respiratory monitoring is initiated. In one embodiment, this is accomplished by putting a belt/strap around the subject's torso which is capable of detecting when the subject takes a breath. It should be appreciated, however, that numerous other means of monitoring the subject's respiratory cycle may be used.

At block 20, the system may be calibrated to take into account the reaction times of the particular subject. In one embodiment this is done by provided a series of test indicators to the subject. The subject is asked to breath each time they receive a test indicator. The time that lapses between when the test indicators are provided and when the subject actually takes a breath is measured for each iteration of the test. Thereafter, some measure of the mean or average reaction time is determined. It should be appreciated that numerous methods may be used to arrive at a reaction time for the subject including, but not limited to, the mean, average, weighted average, etc.

As previously mentioned, we have found that as the respiratory rate is lowered, there is a point at which the heart rate variability pattern, blood pressure rhythm and respiratory rhythms suddenly entrain. In essence, the system shifts modes and operates at its resonance frequency. While in one embodiment, the resonant frequency is approximately 0.1 Hz, in another embodiment it is in the range of between 0.03125 Hertz and 0.234 Hertz.

At block 30, the chosen breath rate indicator may be initialized. Since there are numerous available types of breath indicators, this initialization step will vary depending on the type of breath rate indicator being used. For example, where the breath rate indicator is a belt placed around the subject's torso, initialization would consist of positioning the belt around the subject and initializing the software to operate the indicator functionality.

At this point, the respiratory training sequence may begin by providing the breath rate indicator to the subject (block 40). At block 50 a determination is made as to whether an atypical breathing event has occurred. This may, for example, consist of the subject failing to take a breath within the programmed reaction time after the initial breath indicator was provided. Alternatively, the atypical breathing event may consist of the subject taking multiple breaths between breath indications.

If at block 50 it is determined that an atypical breathing event has not occurred, then the training process continues to block 60 where the timing for the next breath indicator is calculated. In one embodiment, the timing is a function of a predetermined optimal number of breaths and the subject's reaction time from block 20. In another embodiment, the subject's reaction time may be recalculated with each breath indicator to dynamically adjust the timing sequence to more closely follow the current reaction time for the subject. In another embodiment, when no atypical breathing event has occurred, the originally calculated timing sequence (including subject reaction time) is used. In any event, after block 50, the training process returns to block 30 where the next breath indicator is provided to the subject.

If, on the other hand, an atypical breathing event has occurred, then the training process moves to block 70 where the previously determined timing sequence is adjusted to take into account the changed circumstances. Such an adjustment may include, for example, delaying the timing of the next breath indicator where a subject has taken a breath too quickly, or reducing the timing of the next breath indicator where the subject failed to take a breath when previously prompted. In one embodiment, the adjustment made is a function of what the predetermined optimal number of breaths for a given time period is, and how many breaths the subject has taken within that time period. It should of course be appreciated that at any time in the above described training process, the training may be halted by either the subject or an observer.

Figure 2:
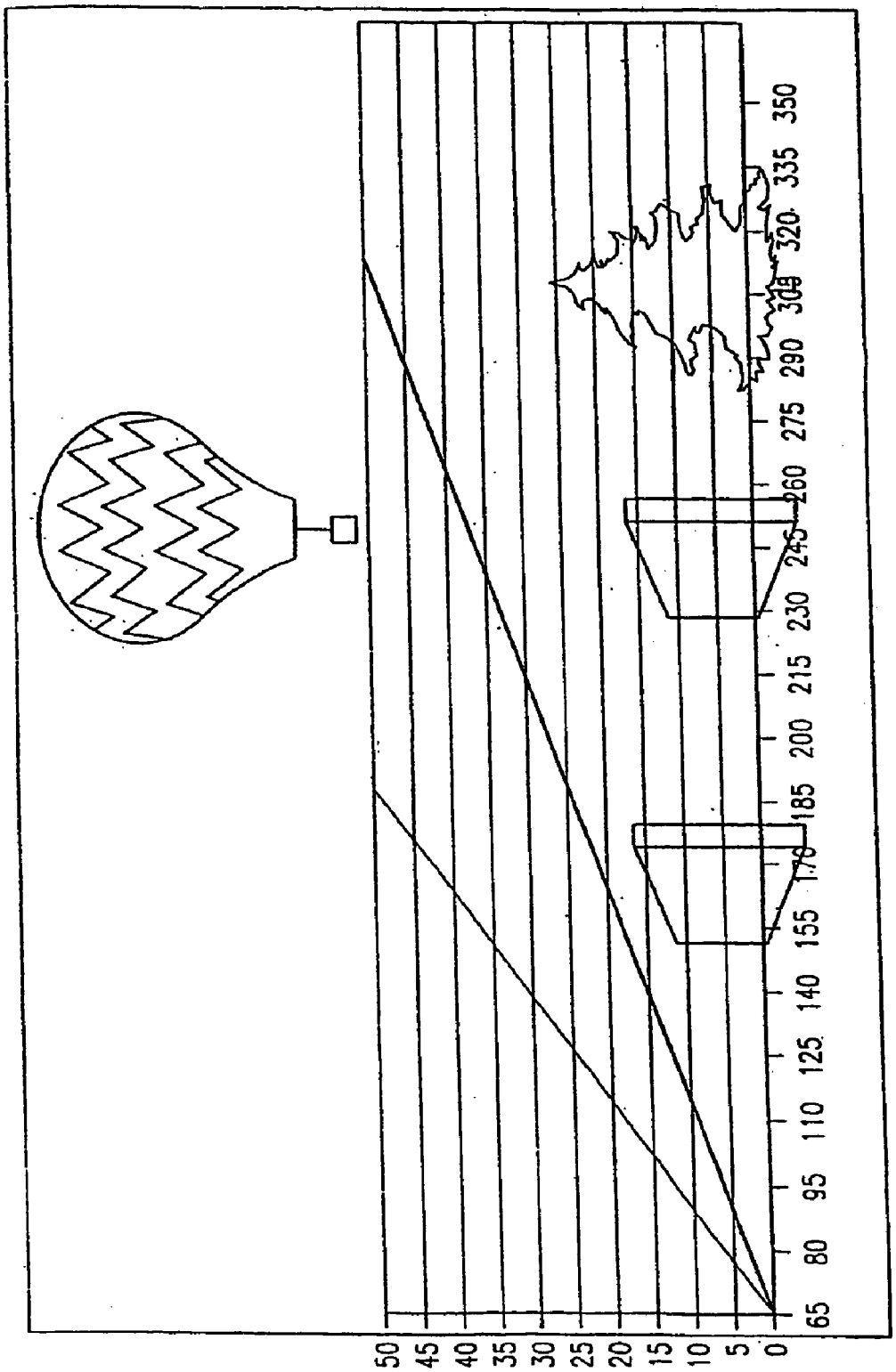
FIG. 2 depicts a positive feedback format according to one embodiment.

In addition to being prompted by the training system's breath indicators, the training system may also provide positive feedback as the subject's respiratory cycle and/or RSA pattern approaches the optimal level. In one embodiment, a graphical element that transitions toward a goal may be displayed to the subject as the optimal breathing level is approached. By way of example, FIG. 2 is a presentation format produced by the training system in accordance with one embodiment of the invention. In this particular embodiment, a hot air balloon floats across a country landscape and the background scenery scrolls slowly by as the balloon floats into the sky based on the individual's entrainment level. If the individual does not maintain the optimal respiratory cycle and/or RSA pattern, the balloon sinks to the ground. Obstacles like a brick wall or a tree, as shown in FIG. 2, are presented during the course of the flight. If the individual's respiratory cycle is not optimized enough to clear one of these obstacles, the balloon's flight is impeded until a sufficiently optimized respiratory cycle and/or RSA pattern is achieved.

Figure 3:
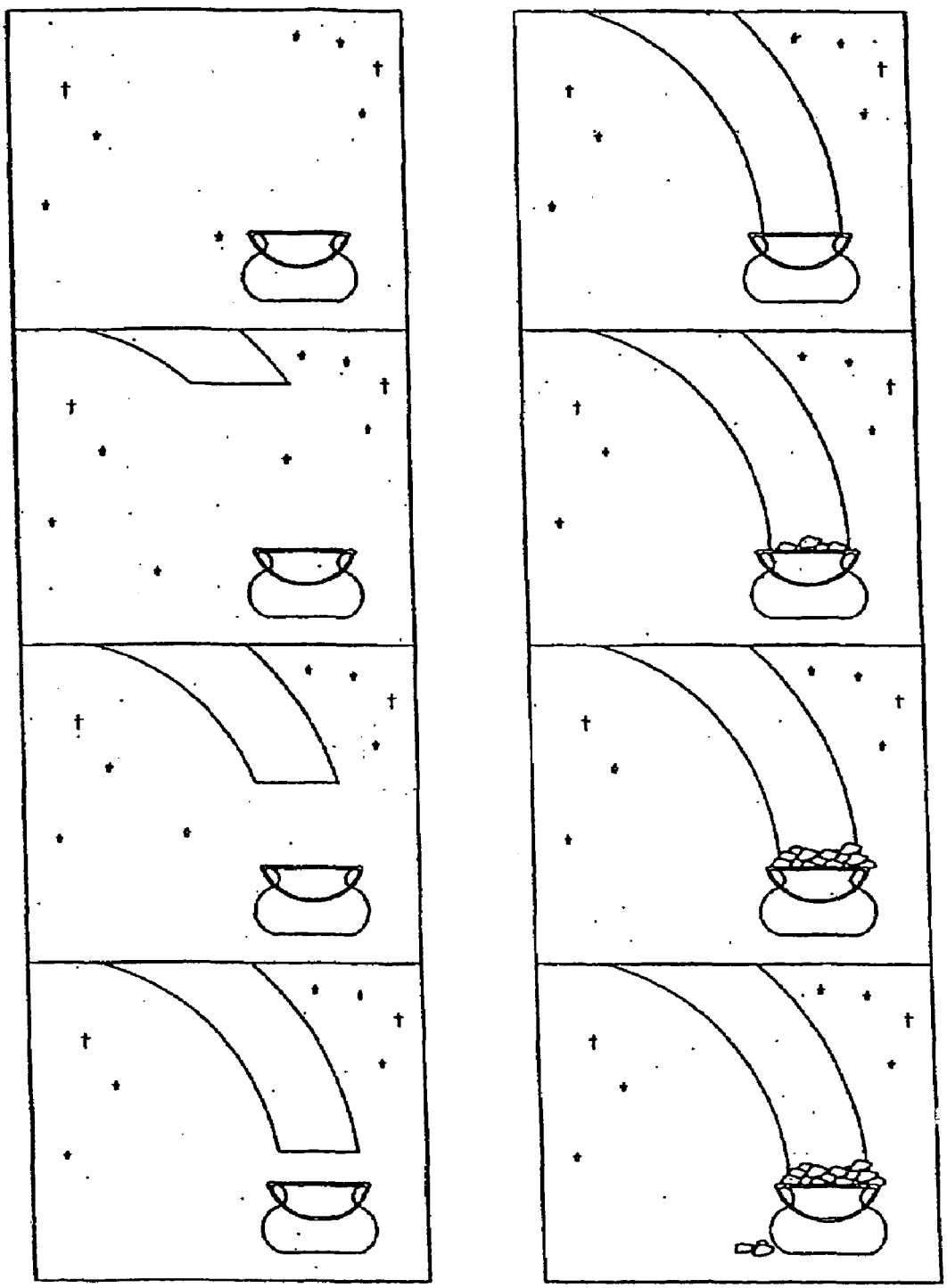
FIG. 3 depicts a positive feedback format according to another embodiment.

FIG. 3 depicts an alternative visual feedback format whereby a rainbow grows toward a pot when an individual's respiratory cycle and/or RSA pattern approaches an optimal level. Growth of the rainbow toward the pot is smooth and steady while the subject maintains internal coherency/entrainment, but the rainbow recedes if the subject does not maintain coherency/entrainment (as determined by the subject's respiratory cycle and/or RSA pattern). Once the rainbow reaches the pot, gold coins accumulate and fill the pot if the subject continues to maintain coherency/entrainment. For example, one coin is added to the pot for each five second time period of medium coherency/entrainment and two coins are added to the pot for each five second time period of high coherency/entrainment.

Figure 4:
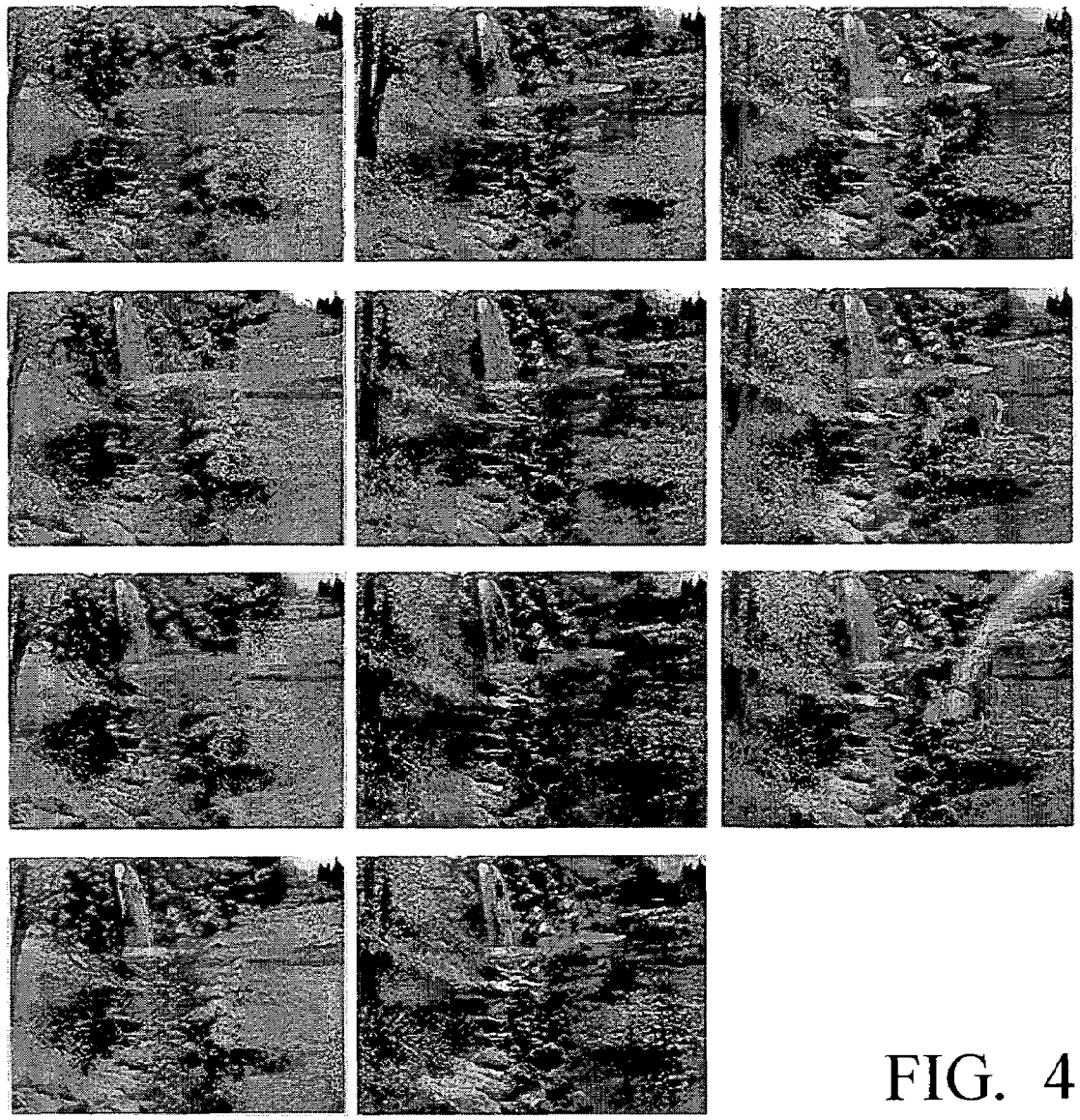
FIG. 4 depicts a positive feedback format according to yet another embodiment.

FIG. 4 is yet another possible visual feedback format produced by the aforementioned training system in accordance with an embodiment of the invention. In this particular embodiment, a nature scene changes with time as the subject maintains an optimized respiratory cycle and/or RSA pattern. In one embodiment, if the quality of the respiratory cycle is low or not maintained, the scene does not change.

As previously mentioned, in another embodiment the visual feedback format may be in the form of a target pattern that is displayed to the subject. In one embodiment, this target pattern is a sine wave of an optimized respiratory/HRV rhythm that the subject's respiratory/HRV rhythm should attempt to match.

In another embodiment, the frequency of the target pattern (e.g., sine wave) moves from a higher frequency to a lower frequency and converges on the optimized frequency as the subject's "coherence peak" is maximized. When the coherence peak reaches its maximum, the frequency would be the natural resonant frequency that would become the target rhythm that may then be displayed to the subject for training purposes.

It should of course be appreciated that numerous other forms of positive feedback may also be provided to the subject as the optimized respiratory cycle and/or RSA pattern is approached. Such other forms of positive feedback may include audible feedback, tactile feedback, etc.

Similarly, as the subject's respiratory cycle and/or RSA pattern moves away from the predetermined optimal level, the graphical element may be transitioned away from the goal. In the embodiment of FIG. 2, the balloon may be caused to transition lower toward the ground. In the alternate embodiment of FIG. 3, the rainbow may begin to lose color and separate from the aforementioned pot of gold. And in the embodiment of FIG. 4, color and detail may be slowly removed from the scene.

Alternate embodiments may employ a variety of display formats including detailed information, graphical information, graphic images, video images, and audio feedback. According to one embodiment, the level of entrainment controls the volume on a music delivery system. This may be implemented based on how close to the optimal respiratory cycle the subject is, where the volume increases as the user's respiratory cycle approaches the optimal level. The system may be optimized by using music especially designed to enhance the entrainment process. Further, in one embodiment, the music changes style and/or pace with entrainment level. Additionally audio controllers may provide verbal messages.

Similarly, coherence, as derived from HRV pattern analysis or respiration rhythms may be used to drive audio, video and/or specific gaming events. In particular, a decrease in coherence (which is associated with a negative mental/emotional state) would generate one type of feedback or gaming event, while an increase in coherence (associated with a positive mental/emotional state) would drive a difference type of feedback or gaming event.

Various images are more helpful in achieving entrainment for an individual than other images. Those images are selected based on predetermined visual and auditory rhythm, and may be specific to the individual and may change from day to day. In one embodiment, a screen saver provides a visual image having a predetermined visual and auditory rhythm, and includes options for the individual to select based on personal preferences. Where feedback is provided to the screensaver program, the screen saver program may perform adjustments to optimize the effects for the individual.

In one embodiment, the training system is implemented in the form of a computer program that can be stored and distributed in a computer-readable medium. The software may be executed on a personal computer, a hand held computing device, or any other medium capable of executing a software program.

Figure 5:
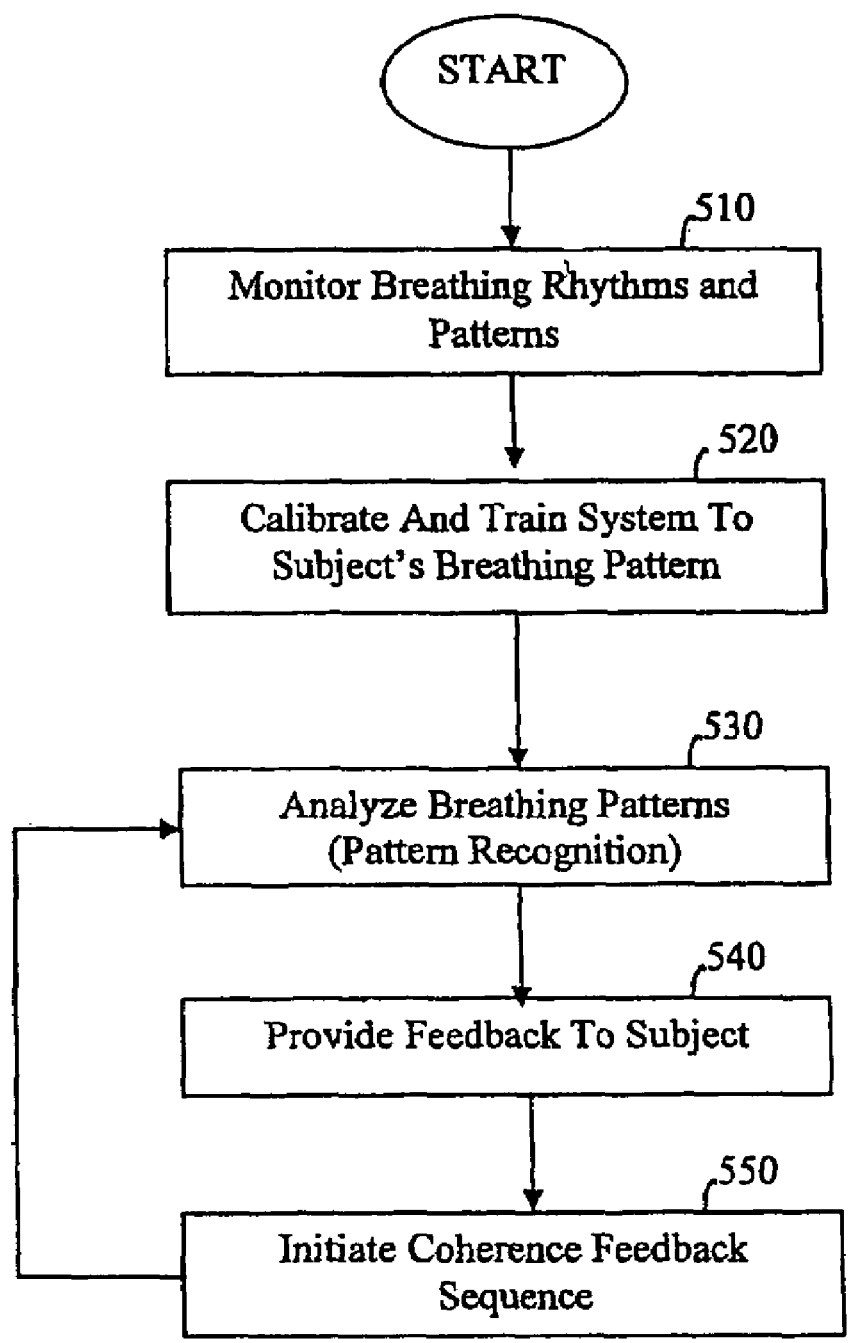
FIG. 5 depicts a flow diagram of a training/feedback process according to one embodiment of the invention.

Illustrated in FIG. 5 is one embodiment for how feedback may be used to improve a subject's emotional state by optimizing their respiratory cycle and/or RSA pattern. In this embodiment, process 500 begins at block 510 where a subject's breathing rhythms and patterns are monitored. In one embodiment, this monitoring proceeds as described above with reference to FIG. 1. The system may then be calibrated to a subject's particular breathing pattern (block 520). This calibration process may be used to adjust the system to take into account a subject's reaction time and/or respiration habits.

With the system monitoring the subject's breathing rhythms, the patterns of the subject's respiration may be analyzed to identify the subject's emotional state (block 530). As will be described below, this information may then in turn be used to optimize the subject's respiratory cycle and/or RSA pattern in a manner that facilitates physiological coherency.

Continuing to refer to FIG. 5, process 500 continues to block 540 where, based on the pattern recognition of block 530, feedback is provided to the subject to reinforce positive emotional states. It should be appreciated that such feedback may be in the form as described above with reference to FIGS. 2–4, or may take on any number of additional presentation formats. However, if a negative emotional state is detected (e.g., emotional stress), at block 550 the system may provide coherence feedback designed to improve the subject's inner emotional state by optimizing the subject's respiratory cycle and/or RSA pattern by, for example, using the above-described feedback approach.

The aforementioned training/feedback system is applicable to the medical community in that the entrained state provides an efficient physiological state, by putting less strain on the glands and organs. By teaching individuals with certain pathologies to self-generate health, the bodies own regenerative systems can be activated and healing facilitated. Applications of the present invention for such use include pain control, blood pressure control, arrhythmia stabilization, diabetic management, as well as many others.

Still additional benefits of reaching and maintaining a state of entrainment include the efficient functioning of the autonomic nervous systems. Moreover, emotional self-management and physiological coherence are effective in reducing depression, anxiety, and other emotional stress, and also in improving glycemic control in diabetic populations. Additionally, maintaining an entrainment state is generally beneficial in treating anxiety, general depression, and other emotional disorders.

The aforementioned training/feedback system is applicable to impulse control, providing training to help overcome eating disorders, anger, and/or addiction. The training/feedback system may also be used in learning stress management and emotional self-management. In one embodiment, a visual display is provided to illustrate other systems within the body, such as neural and hormonal systems, where signals are displayed moving from the heart to the brain, from the lungs to the heart, from the lungs to the brain, etc. Here the effects of these signals are clearly seen, and may be controlled by attaining a state of entrainment.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for improving human emotional states comprising:
   monitoring a subject's respiration;
   determining one or more current breathing patterns for said subject, said one or more current breathing patterns to include at least one of a current respiratory cycle and a current respiratory sinus arrhythmia pattern;
   determining one or more optimal breathing patterns for said subject, said one or more optimal breathing patterns to include at least one of an optimal respiratory cycle and an optimal respiratory sinus arrhythmia pattern, and wherein said one or more optimal breathing patterns induce one or more physiological systems to converge at a resonant frequency which varies over time between about 0.0315 Hertz and 0.234 Hertz;
   prompting said subject to take a breath at a specific time to cause said one or more current breathing patterns to approximate said one or more optimal breathing patterns; and,
   providing feedback to said subject representative of how closely the one or more current breathing patterns approximate the one or more optimal breathing patterns.

2. The method of claim 1 wherein determining said one or more optimal breathing patterns comprises determining said one or more optimal breathing patterns where said one or more optimal breathing patterns are based on heart rate variability.

3. The method of claim 1 wherein prompting comprising prompting said subject to take the breath at the specific time using a breath indicator.

4. The method of claim 3 wherein prompting comprises prompting said subject using said breath indicator where said breath indicator is at least one of a visual indicator, an audio indicator and a tactile indicator.

5. The method of claim 3 further comprising calibrating said breath indicator based on the reaction time of said subject.

6. The method of claim 5 wherein calibrating comprises calibrating said breath indicator dynamically based on the reaction time of said subject such that a timing sequence of said breath indicator adjusts as a function of said subject's reaction time.

7. The method of claim 1 wherein providing feedback comprises providing feedback to said subject where said feedback is a target-oriented visual presentation responsive to said one or more current breathing patterns.

8. The method of claim 7 wherein providing feedback comprises providing feedback to said subject using the target-oriented visual presentation, wherein said target-oriented visual presentation converges on a target pattern as said one or more current breathing patterns converge on said one or more optimal breathing patterns.

9. The method of claim 1 wherein further comprising improving said subject's physiological coherency using said prompting and said providing feedback.

10. The method of claim 1 wherein said one or more current breathing patterns reflect a current emotional state of said subject.

11. The method of claim 1 wherein providing feedback comprises providing feedback to said subject in the form of a gaming event.

12. A system for improving human emotional states comprising:
   a means for monitoring a subject's respiration;
   a means for determining one or more current breathing patterns for said subject, said one or more current breathing patterns to include at least one of a current respiratory cycle and a current respiratory sinus arrhythmia pattern;

a means for determining one or more optimal breathing patterns for said subject, said one or more optimal breathing patterns to include at least one of an optimal respiratory cycle and an optimal respiratory sinus arrhythmia pattern, and wherein said one or more optimal breathing patterns induce one or more physiological systems to converge at a resonant frequency which varies over time between about 0.0315 Hertz and 0.234 Hertz;

a breath indicator to prompt said subject to take a breath at a specific time to cause said one or more current breathing patterns to approximate said one or more optimal breathing patterns; and, a display to provide feedback to said subject representative of how closely the one or more current breathing patterns approximate the one or more optimal breathing patterns.

13. The system of claim 12 wherein said means for determining said one or more optimal breathing patterns comprises means for determining said one or more optimal breathing patterns where said one or more optimal breathing patterns are based on heart rate variability.

14. The system of claim 12 wherein said breath indicator is at least one of a visual indicator, an audio indicator and a tactile indicator.

15. The system of claim 12 wherein said breath indicator is calibrated based on a reaction time of said subject.

16. The system of claim 15 herein said breath indicator is dynamically calibrated based on the reaction time of said subject such that a timing sequence of said breath indicator adjusts as a function of said subject's reaction time.

17. The system of claim 12 herein said display provides feedback in the form of a target-oriented visual presentation responsive to said one or more current breathing patterns.

18. The system of claim 17 herein said target-oriented visual presentation converges on a target pattern as said one or more current breathing patterns converge on said one or more optimal breathing patterns.

19. The system of claim 12 herein said subject's physiological coherency is improved using said breath indicator and said providing feedback.

20. The system of claim 12 wherein said one or more current breathing patterns reflect a current emotional state of said subject.

21. The system of claim 12 wherein said display to provide feedback to said subject comprises a display to provide feedback to said subject wherein said feedback is in the form of a gaming event.

22. A computer program product comprising:
a computer usable medium having computer program code embodied therein, the computer program product having:
computer readable program code to monitor a subject's respiration; p2 computer readable program code to determine one or more current breathing patterns for said subject, said one or more current breathing patterns to include at least one of a current respiratory cycle and a current respiratory sinus arrhythmia pattern;
computer readable program code to determine one or more optimal breathing patterns for said subject, said one or more optimal breathing patterns to include at least one of an optimal respiratory cycle and an optimal respiratory sinus arrhythmia pattern, and wherein said one or more optimal breathing patterns induce one or more physiological systems to converge at a resonant frequency which varies over time between about 0.0315 Hertz and 0.234 Hertz;
computer readable program code to prompt said subject to take a breath at a specific time to cause said one or more current breathing patterns to approximate said one or more optimal breathing patterns; and
computer readable program code to provide feedback to said subject representative of how accurately the one or more current breathing patterns approximate the one or more optimal breathing patterns.

23. The computer program product of claim 22 wherein the computer readable program code to determine said one or more optimal breathing patterns comprises computer readable program code to determine said one or more optimal breathing patterns where said one or more optimal breathing patterns are based on heart rate variability.

24. The computer program product of claim 22 wherein the computer readable program code to prompt comprises computer readable program code to prompt said subject to take the breath at the specific time using a breath indicator.

25. The computer program product of claim 24 wherein the computer readable program code to prompt comprises computer readable program code to prompt said subject using said breath indicator where said breath indicator is at least one of a visual indicator, an audio indicator and a tactile indicator.

26. The computer program product of claim 24 further comprising computer readable program code to calibrate said breath indicator based on the reaction time of said subject.

27. The computer program product of claim 26 wherein said computer readable program code to calibrate said breath indicator comprises computer readable program code to calibrate said breath indicator dynamically based on the reaction time of said subject such that a timing sequence of said breath indicator adjusts as a function of said subject's reaction time.

28. The computer program product of claim 22 wherein said computer readable program code to provide feedback comprises computer readable program code to provide feedback to said subject where said feedback is a target-oriented visual presentation responsive to said one or more current breathing patterns.

29. The computer program product of claim 28 wherein said computer readable program code to provide feedback comprises computer readable program code to provide feedback to said subject using the target-oriented visual presentation, wherein said target-oriented visual presentation converges on a target pattern as said one or more current breathing patterns converge on said one or more optimal breathing patterns.

30. The computer program product of claim 22 further comprising computer readable program code to improve said subject's physiological coherency using said prompting and said providing feedback.

31. The computer program product of claim 22 wherein said one or more current breathing patterns reflect a current emotional state of said subject.

32. The computer program product of claim 22 wherein said computer readable program code to provide feedback to said subject comprises computer readable program code to provide feedback to said subject representative wherein said feedback is in the form of a gaming event.

* * * * *